United States Patent
Dei et al.

(10) Patent No.: US 7,915,248 B2
(45) Date of Patent: Mar. 29, 2011

(54) BORONATED METAL-PHTHALOCYANINES, PROCESS FOR THEIR PREPARATION, PHARMACEUTICAL COMPOSITIONS COMPRISING THEM AND USE THEREOF

(75) Inventors: Donata Dei, San Gimignano (IT); Gabrio Roncucci, Colle Val D'Elsa (IT); Daniele Nistri, Prato (IT); Yann Raoul, Nogent sur Oise (FR); Giacomo Chiti, Montemurlo (IT); Moira Municchi, Pelago (IT); Giulio Jori, Padua (IT)

(73) Assignee: L. Molteni & C. Dei Fratelli Alitti Societa'Di Esercizio S.p.A, Scandicci (IT)

( * ) Notice: Subject to any disclaimer, the term of this patent is extended or adjusted under 35 U.S.C. 154(b) by 701 days.

(21) Appl. No.: 11/662,774

(22) PCT Filed: Sep. 10, 2005

(86) PCT No.: PCT/EP2004/052131
§ 371 (c)(1),
(2), (4) Date: Mar. 12, 2007

(87) PCT Pub. No.: WO2006/027028
PCT Pub. Date: Mar. 16, 2006

(65) Prior Publication Data
US 2008/0004239 A1    Jan. 3, 2008

(51) Int. Cl.
*A01N 55/02* (2006.01)
*A61K 31/555* (2006.01)
*A61K 49/00* (2006.01)
*C07D 487/222* (2006.01)

(52) U.S. Cl. .................... 514/185; 540/145; 424/9.1
(58) Field of Classification Search ............. 540/145; 514/185, 410; 424/9.1
See application file for complete search history.

(56) References Cited

U.S. PATENT DOCUMENTS
3,671,489 A     6/1972   Barnes et al.

OTHER PUBLICATIONS

Pinedo et al., "Translational Research . . . ", The Oncologist 2000,, 5 (suppl1): 1-2 (www.The Oncologist .com).*
McMahon, Gerald, "VEGF Receptor Signaling in Tumor Angiogenesis", The Oncologist 2000; 5(suppl 1): 3-10 (www.The Oncologist.com).*
Kahl et al, "Synthesis and Characterization of a Boranted Metallophthalocyanine for Boron Neutron Capture Therapy," Inorganic Chemistry, 1996, 35, 3878-3880.
Fabris et al., "Photosensitizing properties of a boronated phthalocyanine: studies at the molecular and cellular level," Journal of Photochemistry and Photobiology B: Biology 64 (2001) 1-7.

* cited by examiner

*Primary Examiner* — Paul V. Ward
(74) *Attorney, Agent, or Firm* — Abelman Frayne & Schwab

(57) ABSTRACT

The present invention relates to metal-phthalocyanines bearing at least a group containing boron isotopes $^{11}$B or $^{10}$B, covalently bound to the axial positions of metal-phthalocyanine nucleus; moreover it refers to the process for their preparation, the pharmaceutical compositions comprising them and their use for the treatment of neoplastic and dysplastic pathologies in PDT and/or BNCT.

18 Claims, No Drawings

BORONATED METAL-PHTHALOCYANINES, PROCESS FOR THEIR PREPARATION, PHARMACEUTICAL COMPOSITIONS COMPRISING THEM AND USE THEREOF

This application is a National Phase of PCT/EP 2004/052131, filed Sep. 10, 2004.

FIELD OF THE INVENTION

The present invention relates to metal-phthalocyanines of general formula (I) hereinafter reported, bearing axial ligands containing boron isotopes $^{11}$B or $^{10}$B; moreover it refers to the pharmaceutical compositions comprising them and their use for the treatment of neoplastic and dysplastic pathologies.

STATE OF THE ART

It is known that organic molecules, originating from the phthalocyanines macrocycle complexed with a diamagnetic metal or metaloid and bearing proper substituents, once photo-activated by irradiation with light, are capable of generating reactive oxygen species (ROS).

Such compounds, and, in particular, peripherally substituted Zn(II)-derivatives, have been recently widely described in the scientific literature and in the U.S. Pat. No. 5,965,598, in the European Patent Application No. 906 758 and in the European Patent No. 1 164 135, all in the name of the Applicant, where the use of these molecules in the photodynamic therapy of microbial infections, tumour and proliferative pathologies, as well as in the photodiagnosis and ex vivo sterilization procedures, is claimed, according to their distinctive selectivity for the above mentioned targets. Another important class of photosensitizers consists of axially substituted phthalocyanines, as, for instance, Silicon(IV)-derivatives. These compounds have been extensively studied by M. E. Kenney and co-workers (U.S. Pat. No. 5,166,197; U.S. Pat. No. 5,484,778; U.S. Pat. No. 5,763,602). The derivatives described in the above cited patents and patent applications combine high quantum yields of singlet oxygen production, high absorptions in the red region of visible spectrum and optimum solubility in aqueous medium or formulations, suitable for topical administrations. The side chains, from one side provide the physical-chemical features required for the photosensitizing efficiency, from the other guarantee the high bio-availability of the products, the fast metabolism of the derivatives and thus the final clearance for an optimal localization of the active molecules in the target, thus limiting their toxicity. It is also worth mentioning that the by-products, that may originate from the photobleaching process of the original derivatives after interaction with the light, are not toxic and could facilitate their clearance after the photodynamic treatment, the skin toxicity damage due to a potentially delayed phototoxicity resulting limited.

Moreover, a therapy for the treatment of particularly aggressive neoplastic and displastic pathologies, known as Boron Neutron Capture Therapy (hereinafter called BNCT), has been recently described and is based on the administration of non-radioactive isotope $^{10}$B in conjunction with thermal neutrons. As reported in the state of the art, the interaction of (non-radioactive) $^{10}$B isotope with thermal neutrons generates high linear energy transfer particles such as $^{4}_{2}$He ($\alpha$ particles) and $^{7}_{3}$Li, causing cellular damage through ionization processes at subcellular level. Since those fission fragments have a mean free pathway which is approximately equivalent to the average diameter of mammalian cells, the success of BNCT therapy in the inactivation of tumour or hyperproliferative cells is dependent upon the possibility to achieve a sufficiently large endocellular concentration of boron atoms, that is a consequence of the localization of the carriers they are bound to, in neoplastic or dysplastic tissues.

There is therefore a strong need for the availability of products having both photodynamic enhanced properties and specific cellular and subcellular uptake and bearing substituents with a sufficient number of boron atoms, in order to provide suitable boron concentration in tumour tissues or in areas affected by other pathologies characterised by cell hyperproliferation; such compounds will allow the sequential application of PDT and BNCT with all the advantages of selectivity and activity related to these treatments (Hill J. S. et al. Proc. Natl. Acad. Sci. USA 92 12126-12130). Toward this aim the preparation of the corresponding $^{11}$B-boronated derivatives is also of paramount importance, for the following reasons: 1) as $^{10}$B intermediates are quite expensive and hard to find, the synthetic procedures must be optimised on the products having the natural isotopic abundance; 2) many biological experiments, such as accumulation in tissues, permeability of biological barriers, metabolic pathway determination, etc, can be performed by using $^{11}$B-boronated derivatives in advance; 3) $^{11}$B containing phthalocyanines are themselves useful photosensitizers for PDT applications.

SUMMARY OF THE INVENTION

The Applicant has now surprisingly found that the novel boronated metal-phthalocyanines of general formula (I) hereinafter reported, may be used as photosensitizers in BNCT and PDT therapy. In particular, when bearing substituents containing boron isotopes $^{11}$B, they can be used as photosensitisers for PDT applications, whereas they are efficient for both BNCT and PDT, when bearing one or two axial substituents containing boron isotopes $^{10}$B. These products are able to carry greater amounts of boron than the minimum dose needed for the success of BNCT treatment into the tumour cells, while still showing a high photodynamic efficiency and a selective uptake in rapidly proliferating cells. This finding was unexpected on the light of the previous literature and know-how.

Subject of the present invention are therefore compounds having general formula (I)

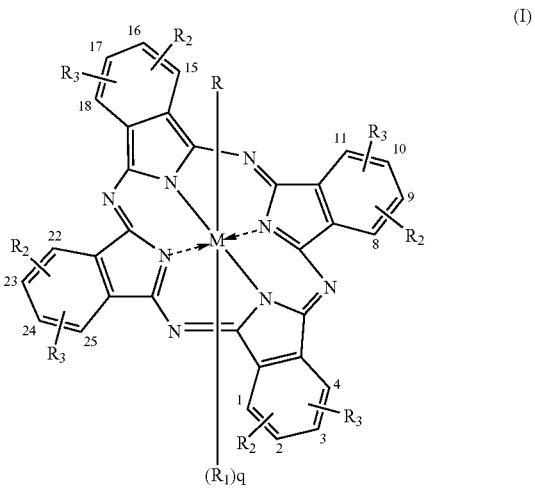

in which

M is chosen in the group consisting of Si, Al and Ge, q is 0 or 1,

R is a group $G\text{-}(Q)_m\text{-}((X)_l\text{-}((Y)_k\text{-}Z)_n)_t$ wherein G is chosen from between O and $O\text{-}Si(CH_3)_2$, Q is selected from the group consisting of T, Ph, $CH_2$-Ph, and triazine, wherein T is selected from among

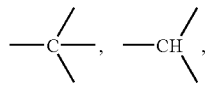

and $-(CH_2)_v-$, and v is an integer comprised between 1 and 5,

X is selected from the group consisting of O, S, T, O-T, S-T, T-O-T, T-S-T, Ph, and O-Ph, wherein T is as defined above, Y is selected from the group consisting of $-(CH_2)_v-$, $O-(CH_2)_v-$, $-(CH_2)_v-O-(CH_2)_v-$, phenyl, O-Ph, Ph-$CH_2$, O-Ph-$CH_2$ and

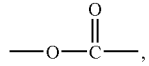

wherein v is as defined above,

Z is a $^{10}B$ or $^{11}B$ boron cluster selected from the group consisting of o,m,p-carboranyl, undecahydro-closo-dodecaboranyl, 1-methyl-o,m,p-carboranyl, undecahydro-closo-dodecaboromercaptyl, nido-7,8-carboranyl, nido-7,9-carboranyl, nido-7,8-methylcarboranyl and bis-p-carboranyl, m is 0 or 1 l is an integer comprised between 0 and 3, k is 0 or 1, n is an integer comprised between 1 and 3, t is an integer comprised between 1 and 3, $R_1$ is selected from a group consisting of R, $CH_3$, OH, O-glucide, $(OCH_2CH_2)_s-OR_4$, and polypeptide, wherein R is as defined above, $R_4$ is selected from the group consisting of H, methyl, and ethyl, and s is an integer comprised between 1 and 10, $R_2$ is chosen from between H and $(W)_p-(OCH_2CH_2)_v-OR_4$, wherein W is selected from $S-(CH_2)_v$, and OPh, p is 0 or 1, v and $R_4$ are as defined above, and $R_3$ is selected from between H and $R_2$, or, when $R_2$ and $R_3$ are in the positions 2, 3, 9, 10, 16, 17, 23, 24, $R_2$ and $R_3$, taken together, are a condensed aromatic nucleus;

provided that:

$R_2$ and $R_3$ are in the positions 1, 4, 8, 11, 15, 18, 22, 25 or 2, 3, 9, 10, 16, 17, 23, 24, when M is Si or Ge, q is 1, and when M is Al, q is 0, and pharmaceutically acceptable salts thereof.

Further subject of the present invention are the pharmaceutical compositions comprising the compounds of general formula (I) as above described, the process for preparing these compounds and their use in PDT and/or BNCT therapy.

Features and advantages of the present invention will be illustrated in details in the following description.

DETAILED DESCRIPTION OF THE INVENTION

According to the present invention with the abbreviation "Ph" a phenyl group is meant.

Preferred compounds according to the invention are boronated silicon-phthalocyanines, i.e. the compounds of formula (I) as above defined in which M is Si.

According to a preferred embodiment of the invention, the present compounds have a general formula (I) in which m is 1, t is 1 and l is 0, thus resulting the substituent R in a group $G\text{-}Q\text{-}((Y)_k\text{-}Z)_n$ wherein G, Q, Y, k and n are as defined above.

By the term "glucide" in the present invention a saccharidic residue is meant, and in particular a residue of mono- or di-saccharides. Examples of glucides according to the invention include, but are not limited to, glucose, galactose, and lactose. Preferably, O-glucide is O-glucose.

According to the invention, by the term "condensed aromatic nucleus" an aromatic group is meant, which forms with the benzene rings of the phthalocyanine nucleus a condensed aromatic group, i.e. an aromatic group in which the two carbon atoms 2,3 and 9,10 and 16,17 and 23,24 are in common for the benzene rings of the phthalocyanine nucleus and the condensed aromatic nucleus. Preferably, the said condensed aromatic nucleus is a benzene ring condensed with the benzene ring of the phthalocyanine nucleus, so to form a naphthalocyanine nucleus.

According to a preferred embodiment of the invention, the group Q is selected from the group consisting of Ph, triazine, $CH_2Ph$, $CH_2$,

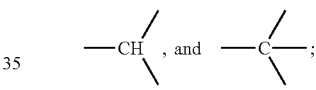

and the group Y is selected from the group consisting of $CH_2$, $OCH_2$, and $CH_2-O-CH_2$. Preferably, the group Z is a $^{10}B$ or $^{11}B$ boron cluster selected from the group consisting of o-carboranyl, 1-methyl-o-carboranyl, nido-7,8-carboranyl, and nido-7,8-methylcarboranyl; and more preferably the group Z is a $^{10}B$ or $^{11}B$ boron cluster selected from the group consisting of o-carboranyl, 1-methyl-o-carboranyl. The present invention allows one to meet the above-mentioned requirements thanks to the compounds of formula (I) as above described. Contrary to what is expected from the molecular structure and taking into consideration that both side chains number and/or bulkiness may interfere with optimal behaviour of the phthalocyanines macrocycle, by reducing the in vivo stability, the photodynamic features and the tumour-localizing properties, the Applicant has surprisingly found that the products subject of the present invention maintain the physical-chemical properties linked with the photosensitizing features, particularly the wavelength, the fluorescence and quantum yield of singlet-oxygen production and the molar extinction coefficient. These products are also able to efficiently localize into tumours after systemic administration and can efficiently sensitise a hard-to-treat tumour, such as the pigmented melanoma, to both PDT and BNCT.

The presence of one or two axial substituents bearing $^{11}B$ or $^{10}B$ isotopes clusters neither interferes with cellular localisation estimated on model cells, nor with the photobleaching processes, while it provides optimal characteristics.

Thanks to the products herein described, a substantial improvement of the specific toxicity on the therapeutic target is achieved for synergic effect, while sparing healthy cells.

Cells may thus be inactivated through a photodynamic mechanism related to the phthalocyanine skeleton and is also possible to inactivate tumour cells by means of BNCT, due to the presence of a sufficiently large number of boron atoms on the phthalocyanine carrier, as well as to the sufficiently high affinity of the boronated phthalocyanine for an experimental tumour model.

Resistance associated to cells mutation and/or transformation as a result of PDT/BNCT combined action is not expected; in fact the cellular inactivation due to photodynamic process is the result of a cellular membrane damage without involvement of the nuclear material; moreover, the inactivation promoted by BNCT is too energetic to induce the selection of radioresistant cell clones.

The Applicant has found that the advantages offered from this class of molecules for the PDT-BNCT application are considerable. In fact, the present phthalocyanines show a highly selective accumulation in tumour tissues. Moreover, the insertion of boron clusters in the axial positions of the macrocycle gives, from a synthetic point of view, the possibility to obtain more tunable compounds with low costs, because the boron clusters can be bound to the phthalocyanine nucleus at the last synthetic step, as better illustrated below. A further advantage of the present compounds bearing one or two multi-boronated chains bound to the metal in the axial positions, is that the amount of boron per molecule is very high despite the fact that only two positions are involved in the linkage with the boronated chains. Furthermore, the amphiphilic properties of the present compounds of formula (I), that are accompanied by higher cellular uptake and greater photocytotoxicity, can be regulated by inserting one or more hydrophilic groups on the phthalocyanine ring and/or on one of the axial position, or by inserting a single axial substituent comprising nido-carboranes.

The process for preparing the present compounds of formula (I) can be based on a convergent synthetic pathway substantially known in the art, comprising the following steps:

i) preparation of the desired axial chain R, $R_1$, modified with an extremity suitably functionalised;

ii) preparation of the metal-phthalocyanine, bearing reactive axial substituents, suitable for reacting with the suitably functionalised extremity of the chains R and $R_1$ coming from step i);

iii) insertion on the metal-phthalocyanine coming from step ii) of the desired suitably functionalised axial chains R, $R_1$, coming from step i), wherein R, $R_1$ are as defined above.

Boronated chains R and $R_1$ bearing 1 to 9 boron clusters can be prepared by using synthetic methods described in literature and well known to any skilled person.

As far as compounds of formula (I) are concerned wherein q is 1 and $R_1$ is different from R, $R_1$ essentially consists of a hydrophilic chain. In this case, minor modifications (protection/deprotection or functionalisation) of commercially available compounds has to be performed to make the chains able to link to the phthalocyanine.

The metal-phthalocyanines bearing reactive axial substituents in step ii) can be for example metal-phthalocyanines bearing Cl, OH or $OCH_3$ axial groups, and can be prepared according to what reported in the literature, for example by a process comprising the following steps a) to c): a) preparation of the appropriate phthalonitrile or 1,3-diiminoisoindoline, b) tetramerization and c) insertion of the metal (possibly one pot with the tetramerization).

Sometimes the reactive species are not isolated (especially in the case of dichloro-Si(IV)-phthalocyanines) and directly reacted with the axial chains.

For the above said compounds of formula (I) bearing different axial groups several steps are requested, however the boronated chain is always inserted at the end of the procedure so that only one deprotection step can follows this step, with the aim to avoid wasting expensive boronated intermediates, especially $^{10}B$ enriched compounds.

In this case the metal phthalocyanine to be functionalised need to have two different axial groups, as for instance $C_1$ and $CH_3$; the boronated chain R is inserted (substitution of the Cl) to give the metal-phthalocyanine axially substituted with the group R on one side and with a group $CH_3$ on the other side. These derivatives are already feasible for the desired application, however can be used as intermediates to prepare metal-phthalocyanines axially substituted with a group R and a group OH. For the preparation of compounds bearing a more complex $R_1$ groups (different from OH or $CH_3$), the $R_1$ hydrophilic group is inserted first on the metal-phthalocyanine substituted with $C_1$ and $CH_3$ to give the metal-phthalocyanine substituted with $R_1$ and $CH_3$; then, by procedures known to any skilled person, the methyl group is converted in OH and the OH is replaced by the boronated chain R. When the symmetrically axially substituted compounds of formula (I) are desired, in which q is 1 and $R_1=R$, their preparation process is the same as above but in step iii) the reactive metal-phthalocyanines are treated with the suitably functionalised chain coming from step i), usually in the presence of a base.

As said above, all the reactions described herein are known in the literature of silicon phthalocyanines (N. L. Oleinick et al., *Photochemistry and Photobiology* 1993, 57(2), 242-247).

The following examples are reported as a non-limiting illustration of the invention.

Example 1

Synthesis of bis(3-o-carboranylpropyl-1-oxy) silicon phthalocyanine

Sodium hydride (0.122 g, 51 mmol) was added to a mixture of silicon phthalocyanine dichloride (0.100 g, 16 mmol) and 3-o-carboranyl-propan-1-ol (0.099 g, 49 mmol) in anhydrous toluene (2 ml). After heating under nitrogen at 80° C. for 72 hours, the mixture was poured into distilled water (20 ml) and extracted three times with toluene (50 ml). The combined organic phases were dried over $Na_2SO_4$ and evaporated to dryness under reduced pressure. Silica gel flash chromatography (petroleum ether/tetrahydrofuran, 3:1) yielded the desired product (0.030 g, 20%). UV-vis ($\lambda_{max}$ in DMF) nm 674. $^1$H-NMR (300 MHz, $CDCl_3$): 9.65 (m, 8H), 8.40 (m, 8H), 2.92-0.84 (bm, 20H), −0.96 (m, 2H), −1.48 (m, 2H), −2.06 (t, 2H). $^{13}$C-NMR (300 MHz, $d_6$-DMSO): 193.7, 157.5, 148.9, 138.8, 136.0, 131.9, 126.5, 126.1, 125.9, 124.9, 122.7, 118.1. ESI$^+$-MS: m/z 943.6 $[C_{42}H_{50}N_8O_2B_{20}Si]^+$ According to the procedure reported in Example 1, the following compounds were obtained:

Example 2

{bis[3,5-bis(o-carboranylmethyloxy)-1-phenoxy]}silicon phthalocyanine

ESI$^+$-MS: m/z 1411.9 $[C_{56}H_{70}B_{40}N_8O_6Si]^+$
UV-vis ($\lambda_{max}$ in DMF): nm 678

Example 3

{[3,5-bis(o-carboranylmethyloxy)-1-phenoxy]methyl}silicon phthalocyanine

ESI$^+$-MS: m/z 993.6 $[C_{45}H_{48}B_{20}N_8O_3Si]^+$
UV-vis ($\lambda_{max}$ in DMF): nm 678

Example 4

{bis[3,5-di(o-carboranylmethyloxy)-1-phenoxy]-1,4,8,11,15,18,22,25-octa[2-(2-ethoxy ethoxy)ethoxy]}silicon phthalocyanine ESI$^+$-MS: m/z 2473.6 $[C_{104}H_{170}B_{40}N_8O_{30}Si]^+$
UV-vis ($\lambda_{max}$ in DMF): nm 749

Example 5

{bis[3,5-di-(m-carboranylmethyl)-2,4,6-triazin-1-yloxy]}silicon phthalocyanine

ESI$^+$-MS: m/z 1357.9 $[C_{50}H_{68}B_{40}N_{14}O_2Si]^+$
UV-vis ($\lambda_{max}$ in DMF): nm 676

Example 6

{[3,5-bis(m-carboranylmethyl)-2,4,6-triazin-1-yloxy]methyl}silicon phthalocyanine ESI$^+$-MS: m/z 964.6 $[C_{42}H_{45}B_{20}N_{11}OSi]^+$
UV-vis ($\lambda_{max}$ in DMF): nm 676

Example 7

{bis[1,3-bis(o-methylcarboranylmethyloxy)-propyl-2-oxy]}silicon phthalocyanine

ESI$^+$-MS: m/z 1348.0 $[C_{50}H_{78}B_{40}N_8O_6Si]^+$
UV-vis ($\lambda_{max}$ in DMF): nm 674

Example 8

{bis{3,5-bis[3,5-di(o-methylcarboranylmethyl)-1-phenoxy]-1-phenoxy}}silicon phthalocyanine ESI$^+$-MS: m/z 2344.9 $[C_{92}H_{138}B_{80}N_8O_6Si]^+$
UV-vis ($\lambda_{max}$ in DMF): nm 680

Example 9

{[1,3-bis(p-carboranyl)-propyl-2-oxy]methyl}silicon phthalocyanine

ESI$^+$-MS: m/z 899.6 $[C_{40}H_{46}B_{20}N_8OSi]^+$
UV-vis ($\lambda_{max}$ in DMF): nm 674

Example 10

{[3,5-bis($^{10}$B-o-carboranylmethyloxy)-1-phenoxy]hydroxy}silicon phthalocyanine ESI$^+$-MS: m/z 980.1 $[C_{44}H_{46}B_{20}N_8O_4Si]^+$
UV-vis ($\lambda_{max}$ in DMF): nm 678

Example 11

{[3,5-bis($^{10}$B-o-carboranylmethyloxy)-1-phenoxy]6-O-α-D-glucopyranosyl}silicon phthalocyanine ESI$^+$-MS: m/z 1142.1 $[C_{50}H_{56}B_{20}N_8O_9Si]^+$
UV-vis ($\lambda_{max}$ in DMF): nm 678

Example 12

{[3,5-bis($^{10}$B-o-carboranylmethyloxy)-1-phenoxy]}{[2-(2-ethoxyethoxy)ethoxy]}silicon phthalocyanine ESI$^+$-MS: m/z 1096.1 $[C_{50}H_{58}B_{20}N_8O_6Si]^+$
UV-vis ($\lambda_{max}$ in DMF): nm 679

Example 13

{bis[3,5-bis($^{10}$B-o-carboranylmethyloxy)-1-phenoxy]}silicon phthalocyanine

ESI$^+$-MS: m/z 1380.9 $[C_{56}H_{70}B_{40}N_8O_6Si]^+$
UV-vis ($\lambda_{max}$ in DMF): nm 680

Example 14

{bis[3,5-bis((2-methyl-$^{10}$B-carboran-1-yl)methyloxy)-1-phenoxy]}silicon phthalocyanine ESI$^+$-MS: m/z 1441.0 $[C_{60}H_{82}B_{40}N_8O_6Si]^+$
UV-vis ($\lambda_{max}$ in DMF): nm 678

Example 15

{bis[3,5-bis((2-methyl-$^{10}$B-carboran-1-yl)methyloxy)-1-phenoxy]-1,4,8,11,15,18,22,25-octa((2-ethoxyethoxy)ethoxy)}silicon phthalocyanine ESI$^+$-MS: m/z 2498.6 $[C_{108}H_{178}B_{40}N_8O_{30}Si]^+$
UV-vis ($\lambda_{max}$ in DMF): nm 749

Example 16

{bis[3,5-bis($^{10}$B-o-carboranylmethyloxy)-1-phenoxy]-1,4,8,11,15,18,22,25-octa[(2-ethoxyethoxy)ethoxy]}silicon phthalocyanine ESI$^+$-MS: m/z 2442.6 $[C_{104}H_{170}B_{40}N_8O_{30}Si]^+$
UV-vis ($\lambda_{max}$ in DMF): nm 749

Example 17

{bis(3-$^{10}$B-o-carboranylpropyl-1-oxy)}silicon phthalocyanine

ESI$^+$-MS: m/z 928.1 $[C_{42}H_{50}B_{20}N_8O_2Si]^+$
UV-vis ($\lambda_{max}$ in DMF): nm 674

Example 18

{bis[3-(2-methyl-$^{10}$B-carboran-1-yl)propyl-1-oxy]}silicon phthalocyanine

ESI$^+$-MS: m/z 956.1 [C$_{44}$H$_{54}$B$_{20}$N$_8$O$_2$Si]$^+$
UV-vis ($\lambda_{max}$ in DMF): nm 674

Example 19

{bis[3-$^{10}$B-o-carboranylpropyl-1-oxy]1,4,8,11,15,18,22,25-octa[(2-ethoxyethoxy)ethoxy]}silicon phthalocyanine ESI$^+$-MS: m/z 956.1 [C$_{90}$H$_{146}$B$_{20}$N$_8$O$_{26}$Si]$^+$
UV-Vis ($\lambda_{max}$ in DMF): nm 745

Example 20 bis(3-o-carboranylpropyl-1-oxy)silicon naphthalocyanine

ESI$^+$-MS: m/z 1143.6 [C$_{58}$H$_{58}$B$_{20}$N$_8$O$_2$Si]$^+$
UV-vis ($\lambda_{max}$ in DMF): nm 770

Example 21 bis(3-$^{10}$B-o-carboranylpropyl-1-oxy)silicon naphthalocyanine

ESI$^+$-MS: m/z 1128.1 [C$_{58}$H$_{58}$B$_{20}$N$_8$O$_2$Si]$^+$
UV-vis ($\lambda_{max}$ in DMF): nm 770

Example 22

{bis[3-(2-methyl-$^{10}$B-carboran-1-yl)propyl-1-oxy]}silicon naphthalocyanine

ESI$^+$-MS: m/z 1156.1 [C$_{60}$H$_{62}$B$_{20}$N$_8$O$_2$Si]$^+$
UV-vis ($\lambda_{max}$ in DMF): nm 770

The invention claimed is:
1. A compound of formula (I)

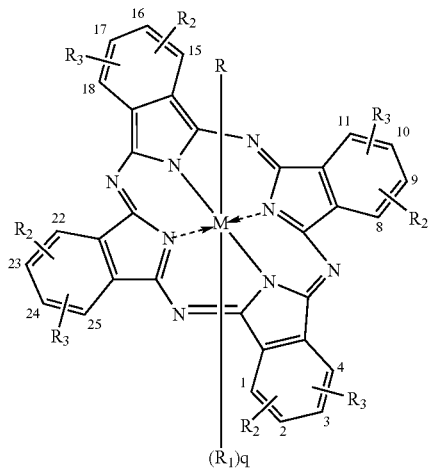

in which
M is selected from the group consisting of Si, Al and Ge,
q is 0 or 1,
R is a group G-(Q)$_m$-((X)$_l$—((Y)$_k$—Z)$_n$)$_t$ wherein
G is selected from the group consisting of O and O—Si(CH$_3$)$_2$,
Q is selected from the group consisting of T, Ph, CH$_2$-Ph, and triazine, wherein T is selected from the group consisting of

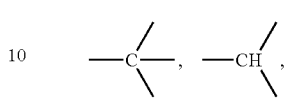

and —(CH$_2$)$_v$—, and v is an integer comprised between 1 and 5,
X is selected from the group consisting of O, S, T, O-T, S-T, T-O-T, T-S-T, Ph, and O-Ph, wherein T is as defined above,
Y is selected from the group consisting of —(CH$_2$)$_v$—, O—(CH$_2$)$_v$—, —(CH$_2$)$_v$—O—(CH$_2$)$_v$—, phenyl, O-Ph, Ph-CH$_2$, O-Ph-CH$_2$ and

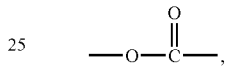

wherein v is as defined above,
Z is a $^{10}$B or $^{11}$B boron cluster selected from the group consisting of o,m,p-carboranyl, undecahydro-closo-dodecaboranyl, 1-methyl-o,m,p-carboranyl, undecahydro-closo-dodecaboromercaptyl, nido-7,8-carboranyl, nido-7,9-carboranyl, nido-7,8-methylcarboranyl and bis-p-carboranyl,
m is 0 or 1,
l is an integer comprised between 0 and 3,
k is 0 or 1,
n is an integer comprised between 1 and 3,
t is an integer comprised between 1 and 3,
R$_1$ is selected from the group consisting of R, CH$_3$, OH, O-glucide,
(OCH$_2$CH$_2$)$_s$—OR$_4$, and polypeptide, wherein R is as defined above, R$_4$ is selected from the group consisting of H, methyl, and ethyl, and s is an integer comprised between 1 and 10,
R$_2$ is selected from the group consisting of H and (W)$_p$—(OCH$_2$CH$_2$)$_v$—OR$_4$, wherein W is selected from the group consisting of S—(CH$_2$)$_v$, and OPh, p is 0 or 1, v and R$_4$ are as defined above, and
R$_3$ is selected from the group consisting of H and R$_2$,
or, when R$_2$ and R$_3$ are in the positions 2,3,9,10,16,17,23,24, R$_2$ and R$_3$, taken together, are a condensed aromatic nucleus;
provided that:
R$_2$ and R$_3$ are in the positions 1,4,8,11,15,18,22,25 or 2,3,9,10,16,17,23,24,
when M is Si or Ge, q is 1, and when M is Al, q is 0,
or a pharmaceutically acceptable salt thereof.
2. The compound according to claim 1, wherein Z is a $^{10}$B boron cluster.
3. The compound according to claim 1, wherein Z is a $^{11}$B boron cluster.
4. The compound according to claim 1, wherein M is Si.
5. The compound according to claim 1, wherein m is 1, t is 1 and l is 0.
6. The compound according to claim 1, wherein said glucide is a residue of mono- or di-saccharides.

7. The compound according to claim 6, wherein said glucide is selected from the group consisting of glucose, galactose, and lactose.

8. The compound according to claim 1, wherein said O-glucide is O-glucose.

9. The compound according to claim 1, wherein the group Z is a $^{10}$B or $^{11}$B boron cluster selected from the group consisting of o-carboranyl, 1-methyl-o-carboranyl, nido-7,8-carboranyl, and nido-7,8-methylcarboranyl.

10. The compound according to claim 9, wherein the group Z is a $^{10}$B or $^{11}$B boron cluster selected from the group consisting of o-carboranyl, and 1-methyl-o-carboranyl.

11. The compound according to claim 1, wherein the group Q is selected from the group consisting of Ph, triazine, CH$_2$Ph, CH$_2$,

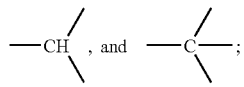

and the group Y is selected from the group consisting of CH$_2$, OCH$_2$, and CH$_2$—O—CH$_2$.

12. The compound according to claim 1, wherein the condensed aromatic nucleus is a benzene ring condensed with the benzene ring of the phthalocyanine nucleus, so to form a naphthalocyanine nucleus.

13. The compound according to claim 1, selected from the following compounds:
bis(3-o-carboranylpropyl-1-oxy) silicon phthalocyanine
{bis[3,5-bis(o-carboranylmethyloxy)-1-phenoxy]} silicon phthalocyanine
{[3,5-bis(o-carboranylmethyloxy)-1-phenoxy]methyl} silicon phthalocyanine
{bis[3,5-di(o-carboranylmethyloxy)-1-phenoxy]-1,4,8,11,15,18,22,25-octa[2-(2-ethoxy ethoxy)ethoxy]} silicon phthalocyanine
{bis[3,5-di-(m-carboranylmethyl)-2,4,6-triazin-1-yloxy]} silicon phthalocyanine
{[3,5-bis(m-carboranylmethyl)-2,4,6-triazin-1-yloxy]methyl} silicon phthalocyanine
{bis[1,3-bis(o-methylcarboranylmethyloxy)-propyl-2-oxy]} silicon phthalocyanine
{bis{3,5-bis[3,5-di(o-methylcarboranylmethyl)-1-phenoxy]-1-phenoxy}} silicon phthalocyanine
{[1,3-bis(p-carboranyl)-propyl-2-oxy]methyl} silicon phthalocyanine
{[3,5-bis($^{10}$B-o-carboranylmethyloxy)-1-phenoxy]hydroxy} silicon phthalocyanine
{[3,5-bis($^{10}$B-o-carboranylmethyloxy)-1-phenoxy] 6-O-α-D-glucopyranosyl} silicon phthalocyanine
{[3,5-bis($^{10}$B-o-carboranylmethyloxy)-1-phenoxy]} {[2-(2-ethoxyethoxy)ethoxy]} silicon phthalocyanine
{bis[3,5-bis($^{10}$B-o-carboranylmethyloxy)-1-phenoxy]} silicon phthalocyanine
{bis[3,5-bis((2-methyl-$^{10}$B-carboran-1-methyloxy)-1-phenoxyl]}silicon phthalo cyanine
{bis[3,5-bis((2-methyl-$^{10}$B-carboran-1-yl)methyloxy)-1-phenoxy]-1,4,8,11,15,18, 22,25-octa((2-ethoxyethoxy)ethoxy)} silicon phthalocyanine
{bis[3,5-bis($^{10}$B-o-carboranylmethyloxy)-1-phenoxy] 1,4,8,11,15,18,22,25-octa[(2-ethoxyethoxy)ethoxy]} silicon phthalocyanine
{bis(3-$^{10}$B-o-carboranylpropyl-1-oxy)} silicon phthalocyanine
{bis[3-(2-methyl-$^{10}$B-carboran-1-yl)propyl-1-oxy]} silicon phthalocyanine
{bis[3-$^{10}$B-o-carboranylpropyl-1-oxy]-1,4,8,11,15,18,22, 25-octa[(2-ethoxy ethoxy)ethoxy]} silicon phthalocyanine
bis(3-o-carboranylpropyl-1-oxy) silicon naphthalocyanine
bis(3-$^{10}$B-o-carboranylpropyl-1-oxy) silicon naphthalocyanine
{bis[3-(2-methyl-$^{10}$B-carboran-1-yl)propyl-1-oxy]} silicon naphthalocyanine.

14. A pharmaceutical composition containing at least one compound of claim 1, or a pharmaceutically acceptable salt thereof.

15. A pharmaceutical composition containing at least one compounds of claim 2, or a pharmaceutically acceptable salt thereof.

16. A diagnostic agent containing at least one compound of claim 1, or a pharmaceutically acceptable salt thereof.

17. A diagnostic method ex vivo/in vivo employing at least one compound of claim 1, or a pharmaceutically acceptable salt thereof.

18. A method for the treatment of a patient suffering from pigmented melanoma tumours, by BNCT therapy, or PDT therapy applied individually, sequentially, or in combination wherein compounds as defined in claim 1 are administered to the patient.

* * * * *

UNITED STATES PATENT AND TRADEMARK OFFICE
CERTIFICATE OF CORRECTION

| | | |
|---|---|---|
| PATENT NO. | : 7,915,248 B2 | Page 1 of 1 |
| APPLICATION NO. | : 11/662774 | |
| DATED | : March 29, 2011 | |
| INVENTOR(S) | : Dei et al. | |

It is certified that error appears in the above-identified patent and that said Letters Patent is hereby corrected as shown below:

On the title page item (22), should read as follows:

(22) PCT Filed: September 10, 2004

Signed and Sealed this
Fourteenth Day of June, 2011

David J. Kappos
*Director of the United States Patent and Trademark Office*